(12) United States Patent
Long

(10) Patent No.: US 7,993,282 B2
(45) Date of Patent: Aug. 9, 2011

(54) TAGGING AND RETRIEVAL OF DNA FROM CASUALTIES

(75) Inventor: Stefan A. Long, El Paso, TX (US)

(73) Assignee: Genetic Testing Laboratories, El Paso, TX (US)

( * ) Notice: Subject to any disclaimer, the term of this patent is extended or adjusted under 35 U.S.C. 154(b) by 1338 days.

(21) Appl. No.: 11/548,094

(22) Filed: Oct. 10, 2006

(65) Prior Publication Data

US 2007/0167957 A1 Jul. 19, 2007

Related U.S. Application Data

(60) Provisional application No. 60/725,866, filed on Oct. 11, 2005.

(51) Int. Cl.
*A61B 10/00* (2006.01)
(52) U.S. Cl. ......... 600/562; 600/564; 600/565; 600/566
(58) Field of Classification Search .......... 600/562–572; 606/167, 170, 180
See application file for complete search history.

(56) References Cited

U.S. PATENT DOCUMENTS

| | | | | |
|---|---|---|---|---|
| 1,260,264 A * | 3/1918 | Huszar | ............................. | 30/130 |
| 4,142,517 A * | 3/1979 | de Stavropoulos et al. | .. | 600/567 |
| 5,040,542 A * | 8/1991 | Gray | ............................. | 600/567 |
| 5,226,890 A * | 7/1993 | Ianniruberto et al. | ... | 604/164.04 |
| 5,515,861 A * | 5/1996 | Smith | ............................. | 600/567 |
| 6,063,037 A * | 5/2000 | Mittermeier et al. | ......... | 600/567 |
| 6,098,724 A * | 8/2000 | Ricker | ............................. | 175/20 |
| 6,155,989 A * | 12/2000 | Collins | ............................. | 600/565 |
| 6,264,618 B1 * | 7/2001 | Landi et al. | ................... | 600/567 |
| 6,502,491 B2 * | 1/2003 | Borowczak et al. | ............ | 83/358 |
| 6,659,338 B1 | 12/2003 | Dittmann et al. | | |
| 6,875,183 B2 | 4/2005 | Cervi | | |
| 2006/0199169 A1 * | 9/2006 | Lam et al. | ......................... | 435/4 |

FOREIGN PATENT DOCUMENTS

| WO | WO-02/39810 | 5/2002 |
|---|---|---|
| WO | WO-02/078431 | 10/2002 |

OTHER PUBLICATIONS

Grassberger, Martin et al., "Evaluation of a novel tagging and tissue preservation system for potential use in forensic sample collection", 10.1016/j.forsciint Feb. 12, 2005, 1-5.

* cited by examiner

*Primary Examiner* — Max Hindenburg
*Assistant Examiner* — Rene Towa
(74) *Attorney, Agent, or Firm* — Janeen Vilven-Doggett; Samantha A. Updegraff; Peacock Myers, P.C.

(57) ABSTRACT

The present invention provides an apparatus and method for collecting a sample (such as, but not limited to, a tissue sample) from a body, such as the body of a casualty, while simultaneously tagging the body with an identifier.

6 Claims, 3 Drawing Sheets

TAGGING AND RETRIEVAL OF DNA FROM CASUALTIES

CROSS-REFERENCES TO RELATED APPLICATIONS

This application claims the benefit of the filing of U.S. Provisional Patent Application Ser. No. 60/725,866, titled "Tagging and Retrieval of DNA from Human Casualties", filed Oct. 11, 2005, and the specification in that application is incorporated herein by reference.

BACKGROUND OF THE INVENTION

1. Field of the Invention (Technical Field)

The present invention relates to the collection of body tissue samples containing, for example, DNA, from human casualties and disposing an identifier on the body or body part.

2. Description of Related Art

Note that where the following discussion refers to a number of publications by author(s) and year of publication, that due to recent publication dates certain publications are not to be considered as prior art vis-a-vis the present invention. Discussion of such publications herein is given for more complete background and is not to be construed as an admission that such publications are prior art for patentability determination purposes.

Casualties of such events as natural disasters, terrorism, and battles often are not identifiable. DNA-based human identity tests are powerful. However, there is no rapid, accurate, and safe means for the collection of DNA samples from casualties. The positive identification of disaster casualties is cumbersome at best. The terrorist attacks on Sep. 11, 2001 in New York, the recent Indonesian tsunami, and hurricane Katrina are examples of the difficulties faced by disaster response teams. DNA analysis is relied upon in routinely and positively identifying victims, casualties, and remains. However, in most cases, the fragile nature of DNA limits its cost effective application of DNA sampling and testing. The collection of samples from corpses in a decayed state also poses serious logistical concerns and poses a biohazard risk to the sample collector.

The following excerpt from *USA Today*, Jan. 13, 2005, D. Leinwand, illustrates the problem:

"Thousands of bodies of tsunami victims are in Buddhist temples across southern Thailand. Most are stacked five high on wooden racks in refrigerated shipping containers. Some are buried near the temples in rows of shallow graves, where cooler temperatures stave off decomposition and maggots can't survive. But for many days before their graves were dug, they lay on the temples' concrete floors in 90-degree heat, which accelerated decomposition and complicated efforts to identify them . . . Behind the screens, Thai bodies have been laid out on concrete slabs as technicians go from corpse to corpse, tagging them with a number, noting their distinctive features and hacking off a piece of bone or extracting a tooth for a DNA sample. On the international side, bodies are placed on steel trays on examination tables. The technicians, doctors and volunteers wear white-plastic suits and gloves and must be decontaminated when they leave the area . . ."

There is no suitable tissue collection device that can simultaneously tag the body of a victim with an identifier that links the body to the tissue sample to be used for DNA isolation. The potential for decomposition of the DNA in corpses requires sampling tissue such as bone marrow that is most likely to remain undenatured. There is a need for such an apparatus and method.

BRIEF SUMMARY OF THE INVENTION

Briefly stated, the present invention provides an apparatus and method for taking a sample from a body and leaving an identifier on the body. Thus, and embodiment of the present invention comprises an apparatus for taking a sample from a body and tagging the body for identification purposes, the apparatus comprising a handle, a coring tube connected to the handle, and a removable identification tag connected to the coring tube.

The identification tag preferably comprises threads. The apparatus preferably further comprises a plunger disposed within the handle for pushing a body sample out of the coring tube. The coring tube preferably comprises a serrated edge. The apparatus preferably further comprises a plunger handle disposed in the handle and a plunger cavity disposed in the handle within which the plunger and the plunger handle may travel. The identification tag preferably comprises an identification component. The apparatus may further comprise a linking component for linking a data device to the identification component.

Another embodiment of the present invention comprises a method for taking a sample from a body and tagging the body for identification purposes, the method comprising connecting a hollow coring tube to an identification tag, inserting the coring tube into the body and bringing a body sample into the coring tube, threading the identification tag into the body, removing the coring tube from the body, and leaving the identification tag in the body. Preferably, inserting the coring tube into the body and threading the identification tag into the body is simultaneous.

The method preferably further comprises threading the identification tag into the body. The method preferably further comprises extracting the sample from the coring tube by pushing a plunger through the coring tube. Inserting the coring tube into the body preferably comprises providing a serrated edge on the coring tube and cutting into the body with the coring tube. The body sample may comprise bone marrow and may comprise DNA. The method may further comprise linking the identification tag to a data device via a linking component.

A primary object of the present invention is to provide for the safe extraction of a body sample while simultaneously tagging the body.

An advantage of the present invention is that it easy to use, requires minimal use of physical force to use, and is capable of complete sampling and tagging within a 1-2 minute timeframe.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into, and form a part of, the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

The present invention provides an apparatus and method for collecting a sample (such as, but not limited, to a tissue sample) from a body while simultaneously leaving an identifier on the body such as, but not limited to, tagging the body with an identifying tag. The present invention aids in disaster remediation, forensic criminology, and military applications, although other applications may be made of the present invention. As used in the specification and claims herein, the terms "a", "an", and "the" mean one or more.

Thus, an embodiment of the present invention provides an apparatus of any given dimensions to accommodate the specific application of the apparatus. Preferably, the dimensions are such that a user can manually operate the apparatus. The apparatus can simultaneously tag a casualty/body and obtain and preserve a sample taken from a body part such as, but not limited to, bone marrow. However, any body component of interest may be sampled and tagged and any item of interest may be obtained and preserved via such sampling such as, but not limited to, DNA.

Figure 1:
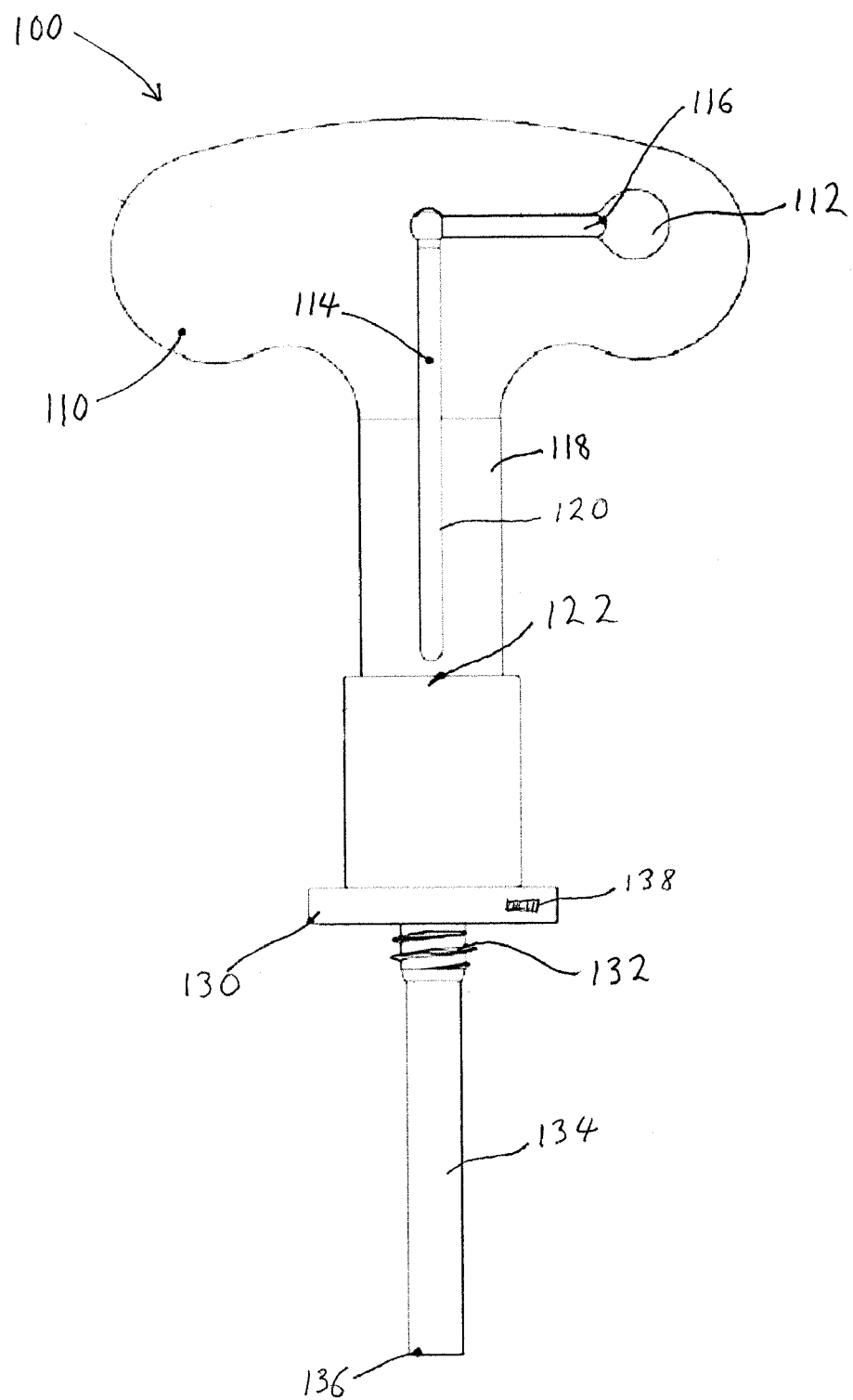
FIG. 1 shows an embodiment of the present invention.
Figure 2:
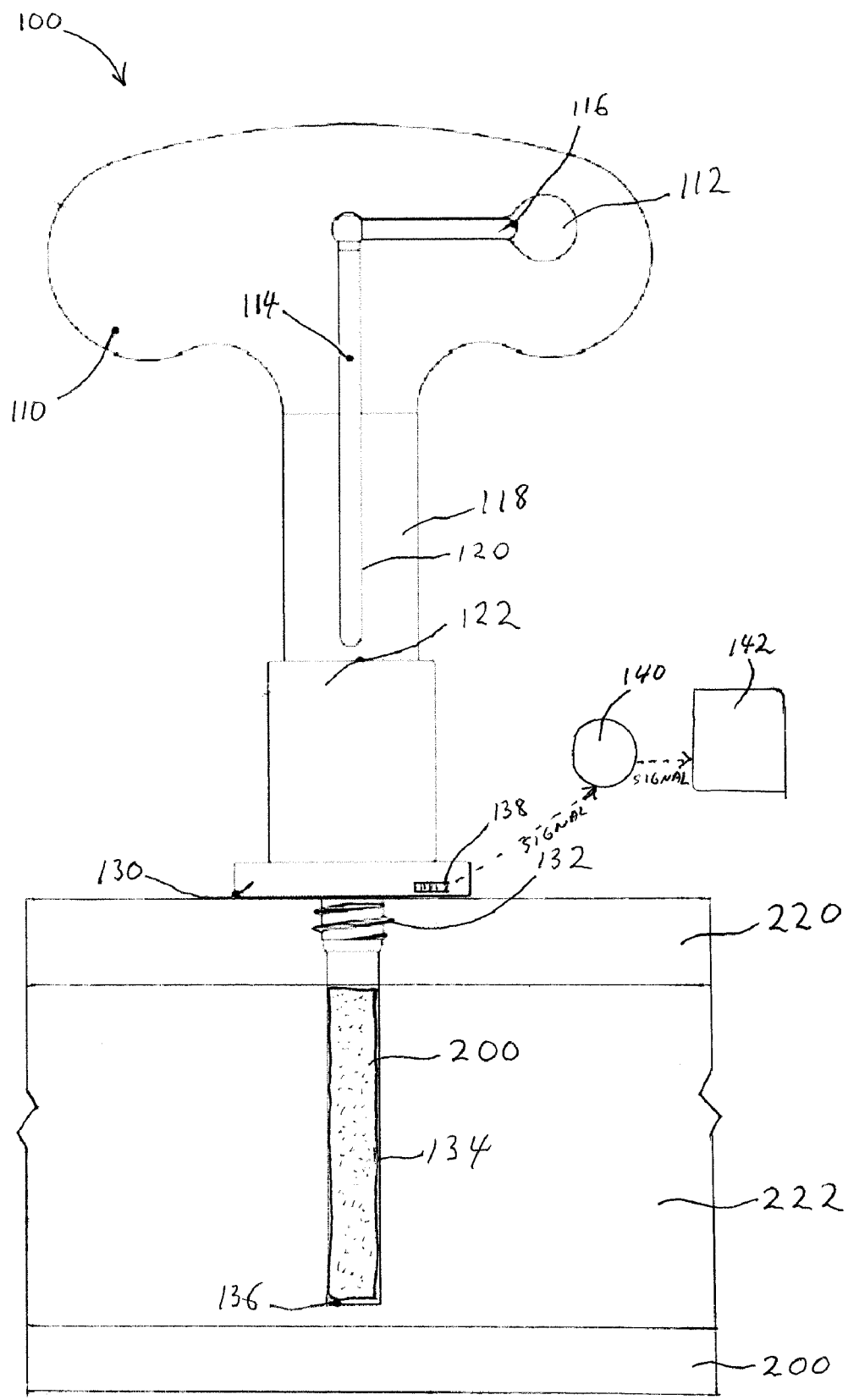
FIG. 2 shows the embodiment of FIG. 1 taking a bone sample.

Referring to the figures, which depict a non-limiting embodiment of the present invention, FIG. 1 shows extraction and tagging apparatus 100 comprising handle 110, body 118, and stop 122, with plunger cavity 120 disposed within both handle 110 and body 118. Attached to stop 122 is identification tag 130, preferably via a triple thread (not shown). Tag 130 comprises self-guided threads 132 to allow threading of tag 130 to a body part such as, but not limited to, bone 220 (shown in FIG. 2). Apparatus 100 also comprises coring tube 134 having serrated edge 136 for cutting into bone 220 so that bone marrow sample 200 can be extracted from bone marrow 222. After sample 200 is taken, tag 130 is left on bone 220. Hollow coring tube 134 extends through the center of tag 130 and through stop 122 so that plunger 114 can travel through coring tube 134 as described below. As shown, handle 110 is preferably of a shape and dimensions to provide leverage for the user as the user turns apparatus 100 to insert coring tube 134 and self-guided threads 132 into bone 220.

Figure 3:
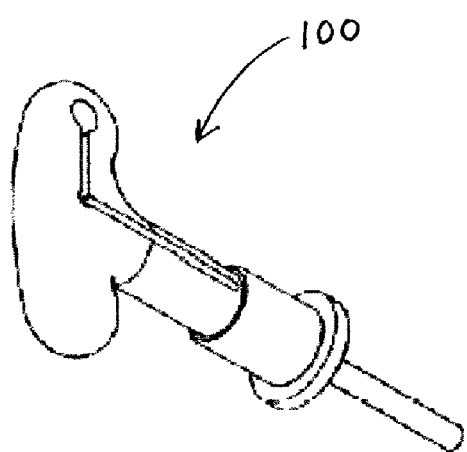
FIG. 3 is a perspective view of the embodiment of FIG. 1.
Figure 4:
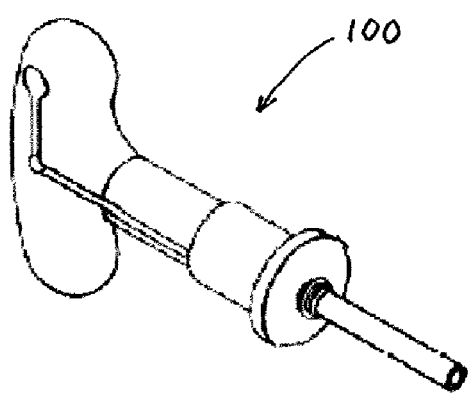
FIG. 4 is another perspective view of the embodiment of FIG. 1.

Plunger 114 and plunger handle 116 is disposed within plunger cavity 120. Plunger cavity 120 extends from the center of handle 110 and body 120 to an outer surface of both. Opening 112 is disposed in handle 110 to allow the user access to plunger handle 116. Thus, plunger handle 116 can be accessed and pushed from opening 112 out and away from handle 110 so that plunger handle 116 and plunger 114 can be pushed down along plunger cavity 120 (which, being open along the outer surface of handle 110 and body 120, permits the travel of plunger handle 116). As plunger 116 is pushed down, it enters coring tube 134 and pushes sample 200 to release sample 200. FIGS. 3 and 4 show perspective views of the embodiment of FIG. 1. Although plunger 114 is used in the embodiment shown, other devices capable of releasing sample 200 from coring tube 134 may be utilized.

Tag 130 can be of any size such as, but not limited to, one square inch and is preferably attached to the sternum bone of the corpse by mechanical energy. Tag 130 is preferably provided with an identification component 138 (such as a barcode or other such identifying component) and can be customized for each application with different, unique shapes and accession numbers/characters. The use of identifying means known in the art such as, but not limited to, scanable barcodes is within the scope of the present invention and helps reduce the chance of error. Apparatus 100 can thus include linking component 140 (e.g., scanner or module) for linking the barcode (i.e., identification component 138) to data recorded on associated data device 142 (e.g., computer) and providing a signal or direct communication link to track critical variables (i.e. information related to casualty body) such as, but not limited to, time of day, gender, location, condition of corpse, clothing, etc.

Thus, in practice, serrated edge 136 of coring tube 134 is used to cut and core into a body part such as bone 220 and marrow 222 to extract marrow sample 200. It is understood that a sample other than bone marrow can similarly be extracted. As coring tube 134 cuts into bone 220, self-guided threads 132 are threaded into bone 220 to attach tag 130 to bone 220. Tag 130 is left in the casualty's body as the remaining components of apparatus 100 are removed. Sample 200 remains in coring tube 134 until, as described above, sample 200 is pushed out of coring tube 134 using plunger 114.

All of the parts of apparatus 100 are made of any material know in the art that is suitable for the applications described herein, particularly rigid material(s). For example, coring tube 134 preferably comprises a metal, more preferably stainless steel.

In another non-limiting embodiment of the present invention, the extraction and tagging apparatus comprises a tag which is held in place via anchors. A trigger energy source is used to drive the body tag via trigger platen and a transfer platen. A sample tube containing a preservation fluid and needle, and a sample tube incorporates a vacuum seal. A depth restriction plate helps position the depth of the needle. A quick snap off region allows the removal of all but the body tag and the anchors after the sample is collected.

In another, non-limiting embodiment, the retrieval of a sample is accomplished through the use of a sternal aspiration needle attached to a custom sample tube similar to a "Yellow Top Vacutainer" containing a suitable preservative. Thus, an embodiment of the present invention comprises such a needle, a sample tube, and a preservative. The sternum marrow is accessed via the same mechanical energy used to apply the identifier tag. Collection and preservation of tissue in this manner is ideal because the collected sample is useful for both conventional serological testing and DNA testing.

Thus, the present invention provides for extracting a body sample from a casualty and tagging the casualty's body with an identifier. Although the present invention has been described as taking a bone marrow sample for isolating and preserving DNA, it is understood that other body parts, tissue, components, etc. may likewise be extracted and identified to the body, and such is within the scope of the present invention.

EXAMPLE

An extraction and tagging apparatus was constructed in accordance with the present invention as depicted in FIGS. 1-4. The apparatus was approximately 8.7 inches long. The handle was approximately 4.5 inches long across the top. The plunger was approximately 2.99 inches long. The coring tube was made of stainless steel and was approximately 3.0 inches long with an approximately 0.25 inch inner diameter.

The preceding examples can be repeated with similar success by substituting the generically or specifically described compositions, biomaterials, devices and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A method for taking a sample from an animal body part and tagging the animal body part for identification purposes, the method comprising:
   inserting an apparatus into the animal body part for taking a sample from the body and tagging the animal body part for identification purposes, the apparatus comprising a handle connected to an apparatus body, a plunger comprising a plunger handle, wherein the plunger and the plunger handle are disposed within the handle and the apparatus body, the apparatus body housing a hollow coring tube;
   the hollow coring tube passing through the apparatus body and through an identification tag removably attached to the apparatus body and bringing an animal body part sample into the hollow coring tube;
   threading the identification tag having a thread into the animal body part:
   wherein the threaded identification tag comprises customized information associated with an animal;
   removing the coring tube from the animal body part;
   extracting the sample from the coring tube by pushing the plunger via the plunger handle through the apparatus body and the coring tube; and
   leaving the identification tag in the animal body part for identification purposes.

2. The method of claim 1 wherein inserting the coring tube into the animal body part and threading the identification tag into the animal body part is simultaneous.

3. The method of claim 1 wherein inserting the coring tube into the animal body part comprises providing a serrated edge on the coring tube and cutting into the animal body part with the coring tube.

4. The method of claim 1 wherein the animal body part sample comprises bone marrow.

5. The method of claim 1 wherein the animal body part sample comprises DNA.

6. The method of claim 1 further comprising linking the identification tag to a data device via a linking component.

* * * * *

UNITED STATES PATENT AND TRADEMARK OFFICE
CERTIFICATE OF CORRECTION

| | | |
|---|---|---|
| PATENT NO. | : 7,993,282 B2 | Page 1 of 1 |
| APPLICATION NO. | : 11/548094 | |
| DATED | : August 9, 2011 | |
| INVENTOR(S) | : Stefan A. Long | |

It is certified that error appears in the above-identified patent and that said Letters Patent is hereby corrected as shown below:

on the Title page of the patent replace item (75) with item (76); and on the Title page of the patent delete Assignee information "(73) Assignee: Genetic Testing Laboratories, El Paso, TX (US)".

Signed and Sealed this
Eighteenth Day of March, 2014

Michelle K. Lee
*Deputy Director of the United States Patent and Trademark Office*